United States Patent [19]

Naim et al.

[11] 4,387,243
[45] Jun. 7, 1983

[54] CONTINUOUS PRODUCTION OF ORTHO-PHTHALIC ACID PRODUCT BY TWO-STEP CATALYTIC NEAT OXIDATION OF LIQUID ORTHO-XYLENE WITH AIR

[75] Inventors: Houssam M. Naim; Nicholas C. Huie; George E. Kuhlmann, all of Naperville, Ill.

[73] Assignee: Standard Oil Company (Indiana), Chicago, Ill.

[21] Appl. No.: 50,159

[22] Filed: Jun. 20, 1979

[51] Int. Cl.$^3$ ............................................. C07C 51/16
[52] U.S. Cl. ................................................ 562/413
[58] Field of Search ........................ 562/413, 414, 416

[56] References Cited

U.S. PATENT DOCUMENTS

| | | | |
|---|---|---|---|
| 2,644,840 | 7/1953 | Roebuck | 562/413 |
| 2,858,334 | 10/1958 | Landau et al. | 562/414 |
| 3,920,735 | 11/1975 | Wampfler et al. | 562/416 |

*Primary Examiner*—Alan Siegel
*Attorney, Agent, or Firm*—Gunar J. Blumberg; William T. McClain; William H. Magidson

[57] ABSTRACT

An improved two-step catalytic neat oxidation of liquid xylene is provided wherein there is no separation of oxidation products from the first oxidation step nor minimum limitation imposed on the liquid o-xylene concentration entering the second step according to the prior two-step oxidations of o-xylene. Rather the first step is conducted under conditions such that the liquid effluent from the first step contains from 6 up to 30 weight percent liquid o-xylene and from 8 up to 40 weight percent o-phthalic acid and such effluent is directly oxidized with air in the second step. By such improved two-step oxidation there is obtained a liquid product containing o-phthalic acid in yields of up to 85–87% of the theoretical yield and also containing impurities separable from o-phthalic acid after it has been converted to its anhydride in vapor form and the anhydride vapors are separated from water vapor. Such two step neat oxidation of liquid o-xylene provides a route to phthalic anhydride commercially competitive with routes starting with the vapor phase oxidation of o-xylene.

10 Claims, No Drawings

CONTINUOUS PRODUCTION OF ORTHO-PHTHALIC ACID PRODUCT BY TWO-STEP CATALYTIC NEAT OXIDATION OF LIQUID ORTHO-XYLENE WITH AIR

TECHNICAL FIELD

This invention relates to the continuous production of an o-phthalic acid product from a two-step catalytic neat oxidation wherein in the first step part of liquid o-xylene is oxidized with air to a liquid mixture containing liquid xylene and oxygen-containing derivatives of o-xylene and said product of the first step is oxidized with air in a second step. More particularly, this invention pertains to the conditions for operating such two-step neat oxidation whereby the total first step liquid oxidation effluent can be fed directly to the second oxidation step and therein oxidized to a liquid product whose o-phthalic acid content represents a yield of at least 80 mole percent based on the o-xylene fed to the first oxidation step.

BACKGROUND ART

U.S. Pat. No. 2,833,816 was the first to disclose the unique catalysis resulting from the combination of a source of bromine and a source of one or more transition, polyvalent metal oxidation catalysts for the liquid phase oxidation with a source of molecular oxygen of di-, tri- and higher alkyl-substituted aromatic compounds (e.g., xylenes, tri- and tetramethyl benzenes) to aromatic di-, tri- and higher carboxylic acids (e.g., phthalic acids and benzene tri- and tetracarboxylic acids). Since such disclosure there has been interest shown from time to time for the use of said catalytic liquid phase oxidation for the conversion of o-xylene to the anhydride of o-phthalic acid.

For example, U.S. Pat. No. 3,402,184 disclosed a continuous process for oxidizing o-xylene in an acetic acid solution containing ions of cobalt, manganese and bromine with air in three steps. Such o-xylene oxidation results in a solution of phthalic anhydride ("PAN") in the acetic acid. Said solution of PAN is combined with water and heated to convert the dissolved PAN to insoluble o-phthalic acid product.

British patent specification No. 856,245 published in 1960 discloses that a single step, neat (no extraneous solvent) oxidation of o-xylene does not go beyond 70 mole percent conversion of the xylene to phthalic anhydride and that a combination of fresh xylene and the 30 percent unoxidized materials cannot be oxidized. Then assuming that a single step oxidation of liquid o-xylene cannot exceed said 70 mole percent yield, said patent devices a two step oxidation wherein compounds having unoxidized alkyl groups still present in the first step reaction mixture are removed before such mixture goes to the second step, the remainder of the first step reaction mixture goes to the second oxidation step and the compounds removed from the first step mixture are returned as part of the feed thereto.

U.S. Pat. No. 3,920,735 discloses that the neat, single step oxidation of o-xylene with air in the presence of cobalt, manganese, zirconium and bromine produces a 60 mole percent yield of phthalic acid together with 0.97 mole percent yield of o-toluic acid, 2.95 mole percent yield of phthalide and 1.88 mole percent yield of 2-carboxybenzaldehyde. Such a PAN product is quite impure and contains a relatively large amount of difficultly removable phthalide.

Copending U.S. patent application Ser. No. 867,050, filed Jan. 5, 1978, describes an improved neat oxidation of o-xylene in the liquid phase to 85 to 92 mole percent yields of o-phthalic acid. The key to such substantially higher yield is to maintain the o-xylene oxidation product as the free dicarboxylic acid; that is, o-phthalic acid, and avoid conditions which permit such acid to dehydrate to its intramolecular anhydride, PAN. Such conditions are the conduct of the neat oxidation of liquid o-xylene with air at a temperature in the range of from 150° C. up to 235° C., at a gauge pressure of from 17 up to at least 28 kg/cm$^2$ and in the presence of from 2 up to 7 weight percent water in the reaction mixture. Satisfactory rates of oxidation are under those conditions, obtained in the presence of catalysis provided on the basis of one gram mole of o-xylene by from 0.3 up to 10 milligram atoms of cobalt, from 0.15 up to 20 milligram atoms of manganese and from 0.225 to less than 60 milligram atoms of bromine. That is, the ratio of gram atom of bromine per gram atom total of cobalt and manganese is at least 0.5:1 but is less than 2:1. Also, when the cobalt concentration is less than 0.75 milligram atom per gram mole of o-xylene, then the difference between the actual cobalt concentration and the 0.75 milligram atom per gram mole of o-xylene can be supplied by zirconium on a gram atom for gram atom basis even though zirconium is not a polyvalent transition metal.

Said higher conversion and yield performing process is illustrated by and is limited to the use of batchwise or semi-continuous operations. By "semi-continuous" operation is meant the type of operation wherein a continuous mode of simultaneously charging air and o-xylene follows the first batchwise mode of charging all of the components of catalysis and water and heating the same to reaction temperature under reaction pressure, at the completion of charging all the xylene continuing only the charging of air until, for all practical purposes, the consumption of oxygen ceases and then stopping the air, and discharging all the reaction mixture for processing to recover the o-phthalic acid product. Heating to reaction temperature of the mixture of water and components of catalysis can be accomplished by heat of reaction released by oxidizing 5 to 25 percent of the o-xylene added with said mixture.

The simple batchwise and the semi-continuous operations of the above copending patent application both provide liquid reaction products containing 89 to 92 weight percent o-phthalic acid. Said simple batchwise operation produces o-phthalic acid in yields of up to 92 mole percent and consumes 5.5 mole percent of o-xylene by total combustion as determined by measurement of the total oxides of carbon produced. Said semi-continuous operation results in an 85 mole percent yield of o-phthalic acid and a 9.7 mole percent total combustion of o-xylene.

The results of said semi-continuous neat air oxidations of o-xylene demonstrate that operating conditions were found to overcome the yield limitation problem of single step oxidation mentioned in British Pat. No. 856,249. Also from the results of said semi-continuous neat air oxidation of o-xylene one would assume that its operating conditions were applicable for successful operation of truly continuous operation with perhaps the added disadvantage of a higher (above 9.7) mole percent total combustion of o-xylene.

However, such assumption, according to copending U.S. patent application Ser. No. 961,763, filed Nov. 17, 1978, was found not to be correct. Said assumption was in error because of the continuous addition of fresh xylene and components of catalysis with the requisite free water and the continuous removal of part of the reaction mixture, continuous operation produces a reaction mixture always containing unreacted xylene. Such difference is in contrast to the batchwise or semi-continuous operations whose reaction mixtures always have a diminishing o-xylene concentration before the reaction mixture is withdrawn from the site of reaction. Such difference in composition of reaction mixture is material because it gives rise to a problem interfering with successful continuous one-step oxidation not found during the development of the successful one-step operation by batchwise or semi-continuous operation.

Manifestation of said problem arising from the presence of unreacted o-xylene begins, we found, when the liquid reaction mixture contains 40 to 41 weight percent o-phthalic acid. Upon reaching such composition, there forms a liquid o-xylene phase and a liquid o-phthalic acid phase which contains the components of catalysis and the requisite 2 to 7 weight percent free water. Said two liquid phases, we found, were immiscible even though the reaction mixture is vigorously stirred. Because the components of catalysis are in the liquid o-phthalic acid phase, the catalysis is not effectively available for rapid oxidation of o-xylene and it accumulates as an increasing immiscible liquid phase. Up to reaching the 40 to 41 weight percent o-phthalic acid concentration, the oxidation reaction is vigorous but, as the immiscible liquid o-xylene accumulates, the oxidation reaction diminishes in vigor until the rate of oxidation becomes commercially unacceptable. Such vigor diminishing condition is readily observable from the volume ratio of o-xylene to water condensed from the exhaust from the oxidation zone. Such volume ratio is normally in the range of from 0.3:1.0 to 0.5:1.0, but the reaction's diminishing vigor is indicated by change of such ratio to 1:1 and finally to 2:1 for an unacceptable reaction rate.

Even when the o-phthalic acid concentration reached 40–41 weight percent in the batchwise and semi-continuous oxidation, there was, it is submitted, sufficient benzoic and o-toluic acid present in the reaction mixture to make miscible the o-xylene and the liquid o-phthalic acid solution of water and catalyst components.

Said U.S. copending application Ser. No. 961,763 filed Nov. 17, 1978 discloses a simple solution to said problem of forming two immiscible liquid phases. Said solution comprises the use of a miscibility aid (e.g., acetic acid or benzoic acid) which then provides a successful continuous single step neat oxidation of o-xylene with substantially complete conversion thereof and produces o-phthalic acid yields of 80 and higher mole percent but at the expense of excessive total combustion of o-xylene and coproduction of high ratio of phthalide to o-phthalic acid of less than 9 mole percent.

We have solved the aforementioned yield and conversion limiting formation of two immiscible liquid phases in a different manner by the use of two neat oxidation steps wherein o-xylene is fed to the first step and is therein converted to a liquid mixture which is directly oxidized per se in the second oxidation step. Our two-step oxidation differs from the two-step oxidation of British Pat. No. 867,050 because our two-step oxidation does not need a separation step to act upon the liquid effluent from the first oxidation step.

There is another prior art two-step air oxidation of a xylene which is disclosed in Canadian Patent No. 817,445. In general, the first step is a neat oxidation of a xylene and the liquid effluent from the first step is oxidized in the second step in the presence of up to 50 weight percent water. Our two step oxidation differs from that of the Canadian patent in that the second step of our process cannot tolerate water concentrations greater than between 7 and 8 weight percent.

According to British Pat. No. 856,245 mentioned before for its two-step neat oxidation, in the first step o-xylene is oxidized with air in the presence of from 0.5 up to 1000, preferably from 5 up to 1000 total miligram atoms of cobalt and manganese per mole of o-xylene with a gram atom ratio of manganese to cobalt of from 2:1 up to 9:1 and either no bromine or up to 15, preferably 4.5, milligram atoms of bromine per gram mole of o-xylene. Also, according to said British patent the feed to the second oxidation step should contain 1.0 weight percent or less of o-xylene. Further, the illustrative example of such two-step oxidation mentions conducting each step until oxygen consumption ceases, a condition indicative of batchwise, not continuous operation.

In our laboratories, we have conducted a first-step air oxidation of o-xylene in the absence of added reaction solvent, in the absence of bromine as a component of catalysis, in the presence of cobalt as the sole component of catalysis and cooling the spent air exhaust therefrom to condense byproduct water and unoxidized xylene without separation thereof for its recycle to the oxidation. By so doing with a cobalt concentration of from 0.5 to 1.0 milligram atoms per gram mole of o-xylene, the continuous air oxidation caused by unacceptably high burning of o-xylene end products as evidence by the total oxides of carbon production of from 0.05 up to 0.1 moles per mole of o-xylene charged. Even then the resulting reaction mixture did not have a xylene content of under 1.0 weight percent but, more undesirably, contained high boiling coproducts predominating in non-precursors of o-phthalic acid which adversely affected both the activity of catalysis and the course of the reaction in the second step conducted continuously.

We also found that the modification of such first continuous air oxidation of o-xylene by the addition of some manganese as a component of catalysis did diminish the co-production of the undesirable high boiling co-products but had little effect on the rate of o-xylene combustion to oxides of carbon. The only effective way we found to decrease the xylene burning rate was to employ some bromine in the continuous first step of air oxidation of liquid o-xylene. To decrease the burning of xylene there is used from 0.5 to 1.0 milligram atom of cobalt per gram mole of o-xylene charged to the continuous first step. This sharply decreased burning of o-xylene in the first step without the use of manganese therein, occurs provided there is also used a cobalt to bromine gram atom ratio of from 1:0.5 up to 1:10.

Such gram atom ratios provide from 0.25 up to 10 milligram atoms of bromine per gram mole of o-xylene charged to the continuous first step. However, such sharp reduction of production of total oxides of carbon still did not provide a reaction mixture of less than one weight percent o-xylene from the continuous first step air oxidation. Adjustment of conditions to lower the o-xylene content of the first step's reaction mixture produced in the presence of cobalt to bromine gram atom ratios of 1:0.5 to 1:10 caused an increase of formation in both total oxides of carbon and the undesirable high boilers which adversely affect catalytic activity and the course of reaction in the continuous second step.

From such experience, we concluded that British Pat. No. 865,245 did not disclose the essential guidance with respect to the successful conduct of a continuous solventless first step air oxidation of o-xylene to a reaction mixture which could be directly oxidized continuously with air to not only a high yield, 80 or more mole percent of o-phthalic acid, but also to a product of such a quality that its impurities were not of a nature to impede recovery of such acid as its anhydride in high yield and purity by commercially feasible techniques.

However, we did find conditions for the continuous conduct of the first step neat oxidation of liquid o-xylene with air to produce liquid reaction mixture which can be, without further processing, fed directly to a second step of continuous liquid phase neat air oxidation, which, when conducted under the conditions we found for the conduct of the second step, provides a high, 80 to 90 mole percent, yield of o-phthalic acid associated with impurities of a character and nature and in an amount which do not interfere with the recovery of the anhydride of phthalic acid in high yield and purity. The success of such a two-step process does not depend upon limiting the o-xylene content of the first step oxidation product to 1.0 weight percent or less as taught by British Pat. No. 856,245, but rather, surprisingly, in view of said patent, the first step liquid reaction mixture can contain up to but not more than 30 weight percent o-xylene and up to but not more than 40 weight percent o-phthalic acid.

Our continuous preparation of o-phthalic acid by two steps of catalytic air oxidation involving the neat oxidation of liquod o-xylene is more specifically described in the sections to follow.

STATEMENT OF THE INVENTION

The present inventive continuous preparation of an o-phthalic acid product having an o-phthalic acid content corresponding to a yield thereof of at least 80 mole percent is obtained by the catalytic liquid phase neat oxidation of o-xylene with air conducted in two steps. In such process the first step is conducted in a stirred oxidation zone operated at a pressure of from 21 up to 29 kg/cm$^2$, at a temperature of from 160° C. up to 225° C., in the presence of liquid water in an amount of from 0.2 up to 7 weight percent of the liquid reaction mixture, with air and xylene being simultaneously fed to the oxidation zone together with an aqueous solution of catalyst system components of cobalt and bromine or cobalt, manganese and bromine as separate streams to provide from 2 to 15 volume percent oxygen in the exhaust from the oxidation zone; for each 1.0 gram mole of o-xylene at least 0.25 milligram atoms of cobalt and as much as 10 milligram atoms of cobalt, at least 0.5 and up to 5 milligram atoms of manganese and at least 0.5 and up to 40 milligram atoms of bromine; and for a residence time such that the reaction mixture contains from 8 up to 40 weight percent o-phthalic acid and from 6 up to 30 weight percent o-xylene. The liquid reaction mixture produced in the first stirred oxidation zone is charged directly and continuously to the second stirred oxidation zone operated at a temperature of from 210° C. up to 230° C., a pressure of from 26.7 kg/cm$^2$ up to 32 kg/cm$^2$ with from 1 up to 7 weight percent water in the reaction mixture in the second oxidation zone, whose reaction mixture also contains an amount of cobalt equal to at least 1.0 milligram atom cobalt per 1.0 gram mole o-xylene charged to the first oxidation zone and a gram atom ratio of Co:Mn:Br of 1:2:3; and an air to first step effluent feed proportion to provide from 5 to 10 volume percent oxygen in the exhaust gas.

In both steps the volume percent oxygen is on a water and xylene and benzoic acid free basis.

Under the foregoing minimum operating conditions for the first and second oxidation steps, the residence time in the second oxidation step is from 3 to 8 times the residence time in the first oxidation step.

More desirable operating conditions for the two sequential oxidation steps are:

|  | First Step | Second Step |
|---|---|---|
| Operating Temperature, °C. | 160 to 205 | 210 to 227 |
| Operating Pressure, kg/cm$^2$ | 25 to 29 | 25 to 29 |
| Co Concentration, mga/gm xylene | 0.5 to 5.0 | 1.0 to 10 |
| o-Xylene Concentration, wt. % | 5 to 29 | — |
| o-Phthalic Acid Concentration, wt. % | 8 to 26 | — |
| Gram Atom Ratio Co:Mn:Br | 1:0.5 to 5:2.2 to 5.5 | — |
| Residence Time, min. | 40 to 80 | 120 to 210 |
| Water Concentration, wt. % | 0.2 to 7 | 1 to 7 |

The preferred operating conditions for the two sequential oxidation steps are:

|  | First Step | Second Step |
|---|---|---|
| Operating Temperature, °C. | 165 to 170 | 212 to 215 |
| Operating Pressure, kg/cm$^2$ | 28 to 29 | 28 to 29 |
| Co Concentration, mga/gm xylene | 0.8 to 1.0 | 1.3 to 1.5 |
| o-Xylene Concentration, wt. % | 6 to 10 | — |
| o-Phthalic Acid Concentration, wt. % | 24 to 28 | — |
| Gram Atom Ratio Co:Mn:Br | 1:0.5 to 2:2.5 to 8 | 2:1 to 2:2.5 to 6 |
| Residence Time, min. | 30 to 50 | 135 to 180 |
| Water Concentration, wt. % | 2 to 4 | 2 to 4 |

The present inventive two-step neat oxidation of liquid o-xylene is sufficiently flexible so that the disadvantages encountered while operating the first step with a water concentration either below the minimum or above the maximum concentrations can be substantially overcome by adjusting the water concentration either of the effluent from the first step by addition of water thereto or by condensing more water from the exhaust from the second step and recycling thereto the extra condensate. The foregoing will be demonstrated in the examples to be presented.

However, operating the second step with either too low or too high a water concentration will result in an incomplete final oxidation as long as such conditions prevail. But as soon as such conditions are ascertained, they can be corrected by changing the temperature to which the exhaust is cooled. Thus, if there is insufficient water in the reaction mixture, the exhaust is cooled to a lower temperature to condense more water therefrom and recycle it to the reaction until the condition has been corrected. After such correction, then the cooling of the exhaust is adjusted to retain the proper amount of water in the reaction mixture. Likewise, to correct the condition of too high a concentration of water in the reaction mixture the exhaust cooling temperature is adjusted upward until the water concentration in the reaction mixture, decreases to the desired level and then the cooling of the exhaust is readjusted so as to retain the proper amount of water in the reaction mixture.

Removal of heat of reaction from each of the two steps of the present inventive process can be accomplished by several commonly used means of indirect heat exchange. For example, heat of reaction can be removed through indirect heat exchange with a cooling liquid circulating in coils in the oxidation zone of the oxidation vessel or in the heat exchange tubes or coils in a heat exchanger outside the oxidation vessel as in the heat exchanger of the thermosiphon loop or in the reflux condenser or in a combination of reflux partial condenser and total condenser. Even when heat of reaction is removed by the first two (internal coils and external thermosiphon) the exhaust (comprising spent air and low boiling compounds such as water, xylene, etc. as vapors) needs to be cooled to return the unoxidized xylene and part of the water as condensate to the reaction zone.

Before providing exemplifications of better and best modes of conduct of the present inventive two-step catalytic neat air oxidation of liquid o-xylene, the adverse effects of too low or high water or catalyst component content of the reaction mixture will be demonstrated for comparison with results from operation within the preferred conditions of the present invention.

In the tabulated data to follow the pressure unit $kg/cm^2$ G is gauge pressure; "Cat. Comp." is used to abbreviate catalyst composition; "2-CBA" is used to designate the compound 2-carboxybenzaldehyde; and "High Boiler" is used as a collective name for all of the group of compounds having an atmosphere pressure boiling point above 300° C.

To determine the feasibility of varying operating conditions for the conduct of the second step neat oxidation, a portion of the effluent from the continuous first step oxidation is isolated and collected in a pressurized vessel and then permitted to cool to ambient temperature (25–27° C.) without decompressing the sample collection vessel. This means for collecting first step effluent was used so that volatile components; e.g., xylene and water would not flash off but rather would be retained. In some cases, more than one of such samples was isolated, collected and cooled so that several second step variations in operating conditions could be compared on a side-by-side basis. The collected first step effluent was then subjected to batchwise oxidation conducted according to prior selected second step operating conditions. In this way the useful second step operating conditions could be studied and their parameters developed. Such first step continuous and second step batchwise neat oxidations produced results which correlated rather well with and thus provided a sound basis for selecting operating conditions for continuous second step oxidation. Moreover, unfavorable results from such batchwise second step operation could avoid large failures and permit changes in continuous second step operating conditions so that more successful results could still be obtained from continuous use of a major proportion of the effluent from the continuous first step oxidation. Such batchwise second step operation also permitted study of ways to operate successfully with first step effluent produced under less favorable conditions caused by operational upsets.

The oxidation reaction apparatus used for the continuous first and second step operations of the examples to follow are each of the stirred tank type and have an internal diameter of 15 cm, a height of 76 cm and a total internal volume of 14 liters. Each vessel is constructed of 9.5 mm thick titanium. Each reaction vessel has an internal coil which can be used to either supply heat to the stirred liquid contents or to remove heat therefrom by indirect heat exchange between a fluid pumped through said coil and the stirred liquid reaction mixture. Each vessel has valved inlets for introducing liquid feed, catalyst solution and one other liquid through flow meters into the upper portion of the vessel; a valved gas inlet for introducing compressed air into the bottom of the stirred reaction mixture; a heat traced valve outlet in the lower portion of the stirred reaction mixture for withdrawal of fluid effluent from the vessel; and a gas outlet in the upper portion of the vessel for withdrawal of exhaust comprising spent air, carbon oxides, water vapor and xylene vapor from the oxidation vessel.

As auxiliary apparatus, there are interconnected to each oxidation vessel a first vertical upflow condenser and a second upflow vertical condenser for series flow therethrough of exhaust gas transferred from its outlet in the oxidation vessel to the bottom inlet of the first vertical condenser. Said first vertical upflow condenser has a mean heat exchanger area of 0.67 $m^2$ and said second vertical condenser has a mean heat exchange area of 0.39 $m^2$. An adjustable pressure control valve is in the gas exit line from the second vertical condenser and said valve is set to control the pressure in the oxidation vessel and the above condensation system. The two condensers each have their own cooling system of cool water or steam which can be supplied at a gauge pressure of from 0 up to 9 $kg/cm^2$. The decompressed exhaust gas substantially free of water and xylene is cooled to remove any remaining water and xylene and then flows to a wet gas test meter with a flow measuring capacity of 13,590 normal liters per hour. Following said meter there are gas sampling lines leading to $CO_2$, CO and $O_2$ analyzers prior to venting the exhaust to the atmosphere.

Thermowells are provided for measurement of temperature of the stirred reaction mixture, and the gas vented from each of the first and second vertical upflow condensers. Means are also provided for measuring the temperature of liquid reflux flowing back to the reaction vessel from the condensers.

From ACM 77—193, Cases 1, 2 & 3

TABLE I

| Description - Xylene Feed: 7.7 and 0% Benzoic Acid | | | |
|---|---|---|---|
| Example | A | B | C |
| Step One Conditions | | | |
| Pressure, $kg/cm^2$ G | 28.1 | 28.1 | 28.1 |
| Temperature Range, °C. | 177–181 | 177–181 | 162–168 |
| Temperature Average, °C. | 179 | 179 | 165 |
| o-Xylene Feed, g/min. | 106* | 106* | 106 |
| Cat. Comp./g. mole feed | | | |
| Co, milligram atom | 1.0 | 1.0 | 1.5 |
| Mn, milligram atom | 2.0 | 2.0 | 0.75 |
| Br, milligram atom | 4.0 | 4.0 | 6.0 |
| Air Rate, nl/min. | 186 | 186 | 210 |
| Residence Time, min. | 55 | 55 | 45 |

TABLE I-continued

Description - Xylene Feed: 7.7 and 0% Benzoic Acid

Step Two Conditions

| | | | |
|---|---|---|---|
| Pressure, kg/cm² G | 28.1 | 28.1 | 28.1 |
| Temperature Range, °C. | 160–230 | 160–227.8 | 160–224 |
| Temperature Average, °C. | 227 | 227 | 215.6 |
| Feed, grams | 600 | 600 | 600 |

Cat. Comp./g. mole feed

| | | | |
|---|---|---|---|
| Co, milligram atom | 1.0 | 1.5 | 2 |
| Mn, milligram atom | 2.0 | 3.0 | 2.75 |
| Br, milligram atom | 4.0 | 4.5 | 7.0 |
| Air Rate, nl/min. | 34 | 34 | 34 |
| Reaction Time, min. | 45 | 41 | 48 |

| Product Analyses, wt. % | Step One | Step Two | Step One | Step Two | Step One | Step Two |
|---|---|---|---|---|---|---|
| Phthalic Acid | 13.42 | 86.6 | 13.42 | 82.7 | 17.6 | 89.6 |
| Water | 2.69 | 4.68 | 2.69 | 4.0 | 5.6 | 4.5 |
| o-Xylene | 20.1 | 0 | 20.1 | 0.02 | 11.3 | 0.16 |
| Benzoic Acid | 7.31 | 6.89 | 7.31 | 5.62 | 0.93 | 1.02 |
| o-Toluic Acid | 28.4 | 0.22 | 28.4 | 0.31 | 33.8 | 1.09 |
| Phthalide | 6.29 | 0 | 6.29 | 0.08 | 6.56 | 0 |
| 2-CBA | 2.5 | 0 | 2.5 | 0.05 | 3.65 | 0 |
| High Boiler | 6.70 | 0.013 | 6.7 | 0.14 | 2.13 | 2.20 |
| Accountability | 92% | 98.6% | 92% | 95.9% | 91.7% | 99.2% |
| Mole % Burned | 4 | 4.6 | 4 | 3.4 | 4.2 | 3.2 |

*Xylene feed also contained 5.3 g/min. benzoic acid.

From ACM 77—193, Cases 9, 10 & 11

TABLE II

Description - NO BENZOIC ACID IN FEED

| Example | D | E | F |
|---|---|---|---|

Step One Conditions

| | | | |
|---|---|---|---|
| Pressure, kg/cm² G | 28.1 | 28.1 | 28.1 |
| Temperature Range, °C. | 162–168 | 181–185 | 181–185 |
| Temperature Average, °C. | 165 | 183 | 183 |
| o-Xylene Feed, g/min. | 106 | 106 | 106 |

Cat. Comp./g. mole feed

| | | | |
|---|---|---|---|
| Co, milligram atom | 1.0 | 0.5 | 0.5 |
| Mn, milligram atom | 0.5 | 0.5 | 0.5 |
| Br, milligram atom | 4.0 | 1.0 | 1.0 |
| Air Rate, nl/min. | 210 | 195 | 195 |
| Residence Time, min. | 45 | 120 | 120 |

Step Two Conditions

| | | | |
|---|---|---|---|
| Pressure, kg/cm² G | 28.1 | 28.1 | 28.1 |
| Temperature Range, °C. | 160–220 | 160–206 | 160–227 |
| Temperature Average, °C. | 210 | 204.4 | 205 |
| Feed, grams | 600 | 600 | 600 |

Cat. Comp./g. mole feed

| | | | |
|---|---|---|---|
| Co, milligram atom | 1.0 | 1.0 | 1.0 |
| Mn, milligram atom | 2.0 | 2.0 | 2.0 |
| Br, milligram atom | 3.0 | 3.0 | 3.0 |
| Air Rate, nl/min. | 34 | 34 | 34 |
| Reaction Time, min. | 60 | 67 | 45 |

| Product Analyses, wt. % | Step One | Step Two | Step One | Step Two | Step One | Step Two* |
|---|---|---|---|---|---|---|
| Phthalic Acid | 13.0 | 74.5 | 22.2 | 84.2 | 22.2 | 22.2 |
| Water | 3.77 | 7.93 | 0.39 | 3.48 | 0.39 | 0.80 |
| o-Xylene | 23.7 | 0.04 | 9.07 | 0.01 | 9.07 | 0.13 |
| Benzoic Acid | 1.1 | 0.91 | 1.28 | 0.96 | 1.28 | 1.25 |
| o-Toluic Acid | 33.1 | 3.28 | 23.6 | 0.28 | 23.6 | 25.5 |
| Phthalide | 4.69 | 5.66 | 7.83 | 0.67 | 5.66 | 11.0 |
| 2-CBA | 3.49 | 2.17 | 2.15 | 0 | 2.17 | 3.37 |
| High Boiler | 6.34 | 0.34 | 13.0 | 0.10 | 0.34 | 3.88 |
| Accountability | 93.2% | 95.2% | 86.5% | 90.5% | 86.5% | 84.2% |
| Mole % Burned | 4.2 | 4.1 | 7.2 | 4.8 | 7.2 | |

*Also 12.9 weight percent phthalic anhydride. Some additional xylene oxidation but unoxidized xylene stripped out.

From ACM 77—193, Cases 23, 24 & 25

TABLE III

Description: XYLENE FEED 10% BENZOIC ACID

| Example | G | H | I |
|---|---|---|---|

Step One Conditions

| | | | |
|---|---|---|---|
| Pressure, kg/cm² G | 19 | 14 | 14 |
| Temperature Range, °C. | 183–189 | 181–185 | 181–185 |
| Temperature Average, °C. | 186 | 183 | 183 |
| o-Xylene Feed, g/min. | 53 | 53 | 53 |

Cat. Comp./g. mole feed

| | | | |
|---|---|---|---|
| Co, milligram atom | 0.5 | 1.0 | 1.0 |
| Mn, milligram atom | 0.5 | 1.0 | 1.0 |
| Br, milligram atom | 1.0 | 2.0 | 2.0 |
| Air Rate, nl/min. | 193 | 189 | 189 |
| Residence Time, min. | 100 | 90 | 90 |

Step Two Conditions

| | | | |
|---|---|---|---|
| Pressure, kg/cm² G | 28.1 | 28.1 | 28.1 |
| Temperature Range, °C. | 160–229 | 160–228 | 160–231 |
| Temperature Average, °C. | 227 | 227 | 227 |
| Feed, grams | 600 | 600 | 600 |

Cat. Comp./g. mole feed

| | | | |
|---|---|---|---|
| Co, milligram atom | 1.5 | 3.0 | 2.0 |
| Mn, milligram atom | 1.5 | 3.0 | 2.0 |
| Br, milligram atom | 3.0 | 4.0 | 3.0 |
| Air Rate, nl/min. | 34 | 34 | 34 |
| Reaction Time, min. | 65 | 45 | 75 |

| Product Analyses, wt. % | Step One | Step Two | Step One | Step Two | Step One | Step Two |
|---|---|---|---|---|---|---|
| Phthalic Anhydride | 1.03 | 19.9 | 9.94 | 15.4 | 9.94 | 10.7 |
| Phthalic Acid | 25.5 | 48.2 | 14.5 | 61.3 | 14.5 | 66.2 |
| Water | 1.17 | 5.58 | 0.19 | 0.62 | 0.19 | 0.99 |
| o-Xylene | 5.22 | 0 | 4.97 | 0.08 | 4.97 | 0.06 |
| Benzoic Acid | 9.43 | 10.6 | 11.5 | 11.7 | 11.5 | 11.6 |
| o-Toluic Acid | 16.8 | 0.39 | 21.1 | 1.13 | 21.1 | 1.16 |
| Phthalide | 7.58 | 0.34 | 9.27 | 0.74 | 9.21 | 0.35 |
| 2-CBA | 1.85 | 0 | 2.49 | 0.20 | 2.49 | 0.02 |
| High Boiler | 8.63 | 0.20 | 9.41 | 0.70 | 9.41 | 0.40 |
| Accountability | 81.9% | 87.5% | 87.6% | 93.3% | 87.6% | 93.5% |
| Mole % Burned | 7 | 4 | 6 | 2.4 | 6 | 3.3 |

From ACM 77—193, Cases 26, 28 & 29

TABLE IV

Description: XYLENE FEED - 10, 0 AND 5% BENZOIC ACID

| Example | J | K* | L |
|---|---|---|---|

Step One Conditions

| | | | |
|---|---|---|---|
| Pressure, kg/cm² G | 14 | 21.1 | 14 |
| Temperature Range, °C. | 181–185 | 187–191 | 187–191 |
| Temperature Average, °C. | 183 | 189 | 189 |
| o-Xylene Feed, g/min. | 54 | 56 | 53 |

Cat. Comp./g. mole feed

| | | | |
|---|---|---|---|
| Co, milligram atom | 1.0 | 5 | 5 |
| Mn, milligram atom | 1.0 | 0 | 0 |
| Br, milligram atom | 2.0 | 0 | 0 |
| Air Rate, nl/min. | 189 | 160 | 163 |
| Residence Time, min. | 90 | 93 | 98 |

Step Two Conditions

| | | | |
|---|---|---|---|
| Pressure, kg/cm² G | 28.1 | 28.1 | 28.1 |
| Temperature Range, °C. | 160–227 | 140.6–217.8 | 140.6–217.8 |
| Temperature Average, °C. | | 215.6 | 215.6 |
| Feed, grams | 600 | 600 | 600 |

Cat. Comp./g. mole feed

| | | | |
|---|---|---|---|
| Co, milligram atom | 2.0 | 9.5 | 9.5 |
| Mn, milligram atom | 2.0 | 4.5 | 4.5 |
| Br, milligram atom | 3.0 | 9.0 | 9.0 |
| Air Rate, nl/min. | 34 | 34 | 34 |
| Reaction Time, min. | 50 | 37 | 38 |

Product Analyses, Step

TABLE IV-continued

Description:
XYLENE FEED - 10, 0 AND 5% BENZOIC ACID

| wt. % | One | Two | One | Two | One | Two |
|---|---|---|---|---|---|---|
| Phthalic Anhydride | 9.94 | 21.2 | 0.41 | 0.30 | 0.20 | 0.39 |
| Phthalic Acid | 14.5 | 10.1 | 20.7 | 74.4 | 25.7 | 74.5 |
| Water | 0.19 | 0.43 | 2.1 | 5.8 | 1.3 | 5.3 |
| o-Xylene | 4.97 | 0.09 | 6.0 | 0.44 | 4.15 | 0.13 |
| Benzoic Acid | 11.5 | 11.8 | 1.87 | 1.70 | 1.94 | 4.77 |
| o-Toluic Acid | 21.1 | 21.1 | 23.8 | 3.18 | 25.8 | 1.49 |
| Phthalide | 9.27 | 10.8 | 9.0 | 1.1 | 9.3 | 2.1 |
| 2-CBA | 2.49 | 2.53 | 2.6 | 0.04 | 2.3 | 0.28 |
| High Boiler | 9.41 | 3.09 | 5.2 | 0 | 5.7 | 0 |
| Accountability Mole | 87.6% | 89.8% | 87.9% | 88.2% | 92.3% | 90.3% |
| % Burned | 6 | 0 | 7 | 2 | 9.3 | 1.7 |

*No benzoic acid added to xylene feed.

From ACM 77—193, Cases 31, 32 & 34

TABLE V

Description:
XYLENE FEED 93%, XYLENE 7%, BENZOIC ACID

| Example | M | N | O |
|---|---|---|---|
| Step One Conditions | | | |
| Pressure, kg/cm² G | 28.1 | 28.1 | 28.1 |
| Temperature Range, °C. | 174–179 | 170–174 | 167–169 |
| Temperature Average, °C. | 176 | 173 | 168 |
| o-Xylene Feed, g/min. | 106 | 106 | 106 |
| Cat. Comp./g. mole feed | | | |
| Co, milligram atom | 1.0 | 1.0 | 1.0 |
| Mn, milligram atom | 2.0 | 0.5 | 0.5 |
| Br, milligram atom | 0.5 | 4.0 | 4.0 |
| Air Rate, nl/min. | 186 | 218 | 218 |
| Residence Time, min. | 50 | 60 | 60 |
| Step Two Conditions | | | |
| Pressure, kg/cm² G | 28.1 | 28.1 | 28.1 |
| Temperature Range, °C. | 160–226.7 | 160–227.8 | 160–226.7 |
| Temperature Average, °C. | 223.3 | 227.2 | 226.7 |
| Feed, grams | 600 | 600 | 600 |
| Cat. Comp./g. mole feed | | | |
| Co, milligram atom | 1.0 | 1.0 | 1.0 |
| Mn, milligram atom | 2.0 | 1.5 | 1.5 |
| Br, milligram atom | 4.0 | 5.0 | 5.0 |
| Air Rate, nl/min. | 34 | 34 | 34 |
| Reaction Time, min. | 60 | 33 | 35 |

| Product Analyses, wt. % | Step One | Step Two | Step One | Step Two | Step One | Step Two |
|---|---|---|---|---|---|---|
| Phthalic Acid | 9.0 | 83.1 | 20.1 | 85.9 | 14.8 | 89.1 |
| Water | 1.7 | 1.1 | 3.85 | 3.56 | 2.57 | 1.36 |
| o-Xylene | 25.2 | 0.02 | 7.50 | 0.02 | 14.1 | 0.03 |
| Benzoic Acid | 8.73 | 7.33 | 8.59 | 8.33 | 7.24 | 7.34 |
| o-Toluic Acid | 2.82 | 0.20 | 26.2 | 0.28 | 29.0 | 0.31 |
| Phthalide | 4.61 | 0 | 7.27 | 0 | 4.12 | 0 |
| 2-CBA | 1.69 | 0 | 5.07 | 0 | 4.35 | 0 |
| High Boiler | 11.7 | 0.34 | 5.33 | 0.35 | 6.21 | 0.21 |
| Accountability Mole | 93.7% | 93.0% | 87.5% | 99.0% | 85.6% | 98.4% |
| % Burned | 4.0 | 4.8 | 4 | 4.2 | 4.0 | 3.1 |

From ACM 77—193, Cases 38, 39 & 40

TABLE VI

Description:
XYLENE FEED-93%, XYLENE-7%, BENZOIC ACID

| Example | P | Q | R |
|---|---|---|---|
| Step One Conditions | | | |
| Pressure, kg/cm² G | 28.1 | 28.1 | 28.1 |
| Temperature Range, °C. | 166–170 | 166–170 | 166–170 |
| Temperature Average, °C. | 168 | 168 | 168 |
| o-Xylene Feed, g/min. | 106 | 106 | 106 |
| Cat. Comp./g. mole feed | | | |
| Co, milligram atom | 1.25 | 1.25 | 1.25 |
| Mn, milligram atom | 0.63 | 0.63 | 0.63 |
| Br, milligram atom | 5.0 | 5.0 | 5.0 |
| Air Rate, nl/min. | 218 | 221 | 221 |
| Residence Time, min. | 55 | 65 | 65 |
| Step Two Conditions | | | |
| Pressure, kg/cm² G | 28.1 | 28.1 | 28.1 |
| Temperature Range, °C. | 160–226.7 | 160–221 | 160–215 |
| Temperature Average, °C. | 223.9 | 210 | 208.3 |
| Feed, grams | 600 | 600 | 600 |
| Cat. Comp./g. mole feed | | | |
| Co, milligram atom | 2.0 | 1.75 | 2.25 |
| Mn, milligram atom | 4.38 | 4.63 | 4.63 |
| Br, milligram atom | 6.13 | 10.0 | 11.00 |
| Air Rate, nl/min. | 34 | 34 | 34 |
| Reaction Time, min. | 38 | 45 | 32 |

| Product Analyses, wt. % | Step One | Step Two | Step One | Step Two | Step One | Step Two |
|---|---|---|---|---|---|---|
| Phthalic Acid | 13.6 | 81.6 | 21.3 | 74.9 | 21.3 | 77.7 |
| Water | 2.93 | 4.94 | 1.12 | 2.01 | 1.12 | 8.18 |
| o-Xylene | 16.4 | 0.01 | 6.13 | 0.09 | 6.13 | 0.02 |
| Benzoic Acid | 7.87 | 7.84 | 9.49 | 8.71 | 9.49 | 8.06 |
| o-Toluic Acid | 32.3 | 0.25 | 32.8 | 1.88 | 32.8 | 0.59 |
| Phthalide | 5.62 | 0.10 | 8.19 | 2.97 | 8.19 | 0.81 |
| 2-CBA | 2.98 | 0 | 4.71 | 1.5 | 4.71 | 0.3 |
| High Boiler | 4.96 | 0.06 | 4.11 | 0 | 4.11 | 0 |
| Accountability Mole | 92.0% | 96.1% | 94.2% | 94.0% | 94.2% | 97.2% |
| % Burned | 4 | 3 | 5 | 2.5 | 5 | 2.5 |

From ACM 77—193, Cases 41, 42 & 43

TABLE VII

Description:
XYLENE FEED - 97% XYLENE, 7% BENZOIC ACID

| Example | S | T | U |
|---|---|---|---|
| Step One Conditions | | | |
| Pressure, kg/cm² G | 28.1 | 28.1 | 28.1 |
| Temperature Range, °C. | 161–164 | 169–173 | 169–173 |
| Temperature Average, °C. | 162 | 171 | 171 |
| o-Xylene Feed, g/min. | 106 | 106 | 106 |
| Cat. Comp./g. mole feed | | | |
| Co, milligram atom | 1.25 | 1.15 | 1.15 |
| Mn, milligram atom | 0.63 | 0.575 | 0.575 |
| Br, milligram atom | 5.0 | 4.60 | 4.60 |
| Air Rate, nl/min. | 218 | 218 | 218 |
| Residence Time, min. | 55 | 55 | 55 |
| Step Two Conditions | | | |
| Pressure, kg/cm² G | 28.1 | 28.1 | 28.1 |
| Temperature Range, °C. | 160–225.5 | 160–225 | 160–204.4 |
| Temperature Average, °C. | 223.9 | 212.8 | 193.3 |
| Feed, grams | 600 | 600 | 600 |
| Cat. Comp./g. mole feed | | | |
| Co, milligram atom | 2.25 | 1.65 | 1.65 |
| Mn, milligram atom | 4.63 | 1.575 | 1.575 |
| Br, milligram atom | 6.5 | 6.1 | 6.1 |
| Air Rate, nl/min. | 34 | 34 | 34 |
| Reaction Time, min. | 46 | 32 | 52 |

| Product Analyses, wt. % | Step One | Step Two | Step One | Step Two | Step One | Step Two |
|---|---|---|---|---|---|---|
| Phthalic Acid | 9.47 | 81.7 | 22.5 | 84.1 | 22.5 | 77.9 |
| Water | 1.5 | 8.6 | 12.7 | 3.4 | 12.7 | 9.6 |
| o-Xylene | 19.1 | 0.04 | 6.14 | 0.01 | 6.14 | 0.01 |
| Benzoic Acid | 8.28 | 7.46 | 6.59 | 6.77 | 6.59 | 7.22 |
| o-Toluic Acid | 30.4 | 0.40 | 25.5 | 0.40 | 25.5 | 0.75 |
| Phthalide | 5.64 | 0.11 | 6.63 | 0 | 6.63 | 0.74 |
| 2-CBA | 2.94 | 0 | 1.91 | 0 | 1.91 | 0 |

TABLE VII-continued

| Description: XYLENE FEED - 97% XYLENE, 7% BENZOIC ACID | | | | | | |
|---|---|---|---|---|---|---|
| High Boiler | 7.58 | 0 | 2.27 | 0 | 2.27 | 0 |
| Accountability Mole | 90.2% | 99.8% | 87.4% | 94.9% | 87.4% | 96.4% |
| % Burned | 3.6 | 3.3 | 4.5 | 2.7 | 4.5 | 3.7 |

From 22 May 1977 Memo, Cases II and IV

TABLE VIII

| Description: XYLENE FEED - 93% XYLENE, 7% BENZOIC ACID | | |
|---|---|---|
| Example | No. 1 | V |
| Step One Conditions | | |
| Pressure, kg/cm² G | 28.1 | 28.1 |
| Temperature °C. | 168.3 | 171.1 |
| O₂ in Exhaust, Vol. % | 7 | 6.6 |
| o-Xylene Feed, g/min. | 109.7 | 109.7 |
| Cat. Comp./g. mole feed | | |
| Co, milligram atom | 0.95 | 0.84 |
| Mn, milligram atom | 0.45 | 1.68 |
| Br, milligram atom | 3.8 | 3.8 |
| Air Rate, nl/min. | 209.6 | 178.4 |
| Residence Time, min. | 60 | 60 |
| Step Two Conditions | | |
| Pressure, kg/cm² G | 27.8 | 28.1 |
| Temperature Average, °C. | 215.6 | 215.6 |
| Feed Rate, g/min. | 29.5 | 43.9 |
| Cat. Comp./g. mole feed | | |
| Co, milligram atom | 1.67 | 1.38 |
| Mn, milligram atom | 1.59 | 2.97 |
| Br, milligram atom | 4.90 | 4.08 |
| Air Rate, nl/min. | 56.6 | 56.6 |
| Residence Time, min. | 150 | 103 |
| O₂ in Exhaust, Vol. % | 8 | 9.4 |

| Product Analyses, wt. % | Step One | Step Two | Step One | Step Two |
|---|---|---|---|---|
| Phthalic Acid | 16.9 | 86.3 | 8.2 | 34.4 |
| Water | 2.0 | 3.7 | 4.1 | 8.7 |
| o-Xylene | 7.8 | 0 | 24.9 | 1.5 |
| Benzoic Acid | 8.8 | 6.32 | 8.3 | 7.8 |
| o-Toluic Acid | 37.7 | 0.73 | 26.0 | 20.8 |
| Phthalide | 6.4 | 0.61 | 4.38 | 6.4 |
| 2-CBA | 2.5 | 0.27 | 2.30 | 5.0 |
| High Boiler | 8.6 | 0.22 | 3.84 | 3.0 |
| Mole % Burned | 4.1 | 4.6 | 3.5 | 3.63 |

In the tables before and to be after presented there are reported "High Boiler" components of the effluents from the first and second oxidation steps. Such "High Boilers" have, in general, been previously identified as compounds boiling above 300° C. Such designation is only a matter of convenient general characterization of these coproduced products as a group and is not to be understood as indicating that the "High Boilers" components from the first step are identical with the "High Boilers" components from the second step because such components are not totally identical. We have concluded from chromatographic and mass spectral analyses that the "High Boilers" are formed by (a) oxygen starvation resulting in dixylyl like compounds, (b) decarboxylation resulting in biphenyl carboxylic acids, and (c) dehydration resulting in esters and carboxybenzophenones.

The fluid effluent from the first step oxidation can contain up to 12 weight percent, e.g., from 2 up to 12 weight percent of such "High Boilers." The first step "High Boilers" have been found to be for the most part 2-methylbenzyl esters of o-toluic acid, phthalic acid, benzoic acid, and acetic acid (anion from source of metal oxidation catalyst component). But, in spite of the use of a substantial excess of air, even the dixylyl dimer of o-xylene:1,2-di(o-methylphenyl) ethane, can also be present in the fluid effluent from the continuous first step neat oxidation of liquid o-xylene. The aforementioned analytical procedures indicate that said esters and dixylyl disappear in the second oxidation step and are apparently oxidized to o-phthalic acid. Hence, the first step "High Boilers" do not represent a source of significant ultimate o-phthalic acid yield loss.

The "High Boilers" appearing in the fluid effluent from the second step neat oxidation are of the benzophenone- and biphenyl-carboxylic acid types which resist further oxidation, especially oxidation to o-phthalic acid, and definitely represent an o-phthalic acid yield loss from consumed o-xylene.

The formation of o-phthalic acid, its simple precursors and coproduct "High Boilers" and disappearance of said precursors and early formed "High Boilers" can be illustrated by the oxidations conducted for various periods of time with the same feed containing 530 grams of o-xylene and 100 grams of benzoic acid at a temperature of 227.8° C.; under 28 kg/cm² G (Gauge) pressure; in the presence of the catalyst system provided by 5.0 milligram atoms of cobalt, 10.0 milligram atoms of manganese and 15 milligram atoms of bromine solubilized in the feed by the addition of 10 grams of water; and with the air rate input of 34 nl air per minute. The reaction time for each oxidation and the results thereof are shown in TABLE IX to follow. In said table, the methyl group is abbreviated "Me."

TABLE IX

PROGRESSIVELY LONGER OXIDATIONS OF ORTHO XYLENE

| Reaction Time, min. | 5 | 10 | 20 | 30 |
|---|---|---|---|---|
| Effluent Weight, g. | 651 | 674 | 718 | 685 |
| Effluent Components, g. | | | | |
| Water | 20 | 38 | 59 | 52 |
| o-Xylene | 400 | 324 | 190 | 64 |
| o-Toluic Acid | 54 | 114 | 189 | 229 |
| Phthalide | 4.1 | 9.8 | 24.7 | 41.8 |
| 2-Carboxybenzaldehyde | 1.8 | 3.8 | 11.3 | 17.0 |
| o-Phthalic Acid | 3.1 | 8.7 | 28 | 63 |
| Benzoic Acid | 100 | 96 | 94 | 93 |
| Dixylyl | 3.6 | 11.1 | 12.2 | 20.4 |
| 2-MeBenzyl Acetate | 3.3 | 3.3 | 7.4 | 3.5 |
| 2-MeBenzyl Benzoate | 11.3 | 18.3 | 17.9 | 14.6 |
| 2-MeBenzyl o-Toluate | 2.5 | 5.5 | 7.9 | 14.8 |
| 2-MeBenzyl o-Phthalate[1] | 0.6 | 1.2 | 4.7 | 3.8 |
| Tricarboxybenzophenone | 0 | 0 | 0 | (2) |
| Tricarboxybiphenyl | 0 | 0 | 0 | (2) |

| Reaction Time, min. | 40 | 50 | 75 |
|---|---|---|---|
| Effluent Weight, g. | 676 | 676 | 753 |
| Effluent Components, g. | | | |
| Water | 83 | 37 | 46 |
| o-Xylene | 3.7 | 0.64 | 0.1 |
| o-Toluic Acid | 225 | 175 | 0.52 |
| Phthalide | 68.5 | 71.4 | 2.0 |
| 2-Carboxybenzaldehyde | 26.2 | 34.3 | 0.1 |
| o-Phthalic Acid | 130 | 202 | 569 |
| Benzoic Acid | 97 | 101 | 105 |
| Dixylyl | 12 | 1.8 | 0 |
| 2-MeBenzyl Acetate | 3.2 | 0.7 | 0 |
| 2-MeBenzyl Benzoate | 5.1 | 1.1 | 0 |
| 2-MeBenzyl o-Toluate | 10.7 | 1.6 | 0 |
| 2-MeBenzyl o-Phthalate[1] | 0.23 | 0.71 | 0 |
| Tricarboxybenzophenone | 0.45 | 0.93 | 9.3 |
| Tricarboxybiphenyl | (2) | (2) | 4.9 |

[1] Monoester
[2] Trace

Further illustrations of the differences between "High Boilers" in the first step effluent and in the second step effluent are shown in the table to follow.

(ACM 78—45, TABLE D)

TABLE X

CHARACTERISTIC
FIRST AND SECOND STEP HIGH BOILERS

| Component, wt. % | First Step | Second Step |
|---|---|---|
| Dixylyl | 0.44 to 0.97 | 0 |
| 2-Methylbenzyl Acetate | 0.19 to 0.80 | 0 |
| 2-Methylbenzyl Benzoate | 0.17 to 0.58 | 0 |
| 2-Methylbenzyl o-Toluate | 0.30 to 0.73 | 0 |
| Mono-(2-Methylbenzyl)-Phthalate | 2.9 to 5.6 | 0 |
| Tricarboxybenzenes | Trace | 0.03 to 0.23 |
| Dicarboxybiphenyls | Trace | 0.014 to 0.064 |
| Tricarboxybiphenyls | Trace | 0.68 to 1.19 |
| Dicarboxybenzophenone | | 0.008 to 0.02 |
| Dicarboxyfluorenone | | 0.07 to 0.09 |
| Tricarboxybenzophenone | | 0.57 to 0.58 |
| Tetracarboxybiphenyl | | 0.196 to 0.91 |

From Tables II & III, ACM 77—257

TABLE XI

Description:
XYLENE FEED - 93% XYLENE, 7% BENZOIC ACID

| Example | W | No. 2 |
|---|---|---|
| Step One Conditions | | |
| Pressure, kg/cm$^2$ G | 28.1 | 28.1 |
| Temperature °C. | 187.8 | 165.6 |
| O$_2$ in Exhaust, vol. % | 10 | 2.5 |
| o-Xylene Feed, g/min. | 54.5 | 109.7 |
| Cat. Comp./g. mole feed | | |
| Co, milligram atom | 0.54 | 1.51 |
| Mn, milligram atom | 0.56 | 0.81 |
| Br, milligram atom | 0.80 | 6.04 |
| Air Rate, nl/min. | 201 | 214.3 |
| Residence Time, min. | 75 | 54 |
| Step Two Conditions | | |
| Pressure, kg/cm$^2$ G | 28.1 | 26.7 |
| Temperature °C. | 230 | 212.8 |
| O$_2$ in Exhaust, vol. % | 9.5 | 8.1 |
| Feed rate, g/min. | 20 | 37.8 |
| Cat. Comp./g. mole feed | | |
| Co, milligram atom | 2.52 | 2.05 |
| Mn, milligram atom | 2.68 | 3.12 |
| Br, milligram atom | 3.71 | 6.2 |
| Air Rate, nl/min. | 43.9 | 61.4 |
| Residence Time, min. | 160 | 138 |

| Product Analyses, wt. % | Step One | Step Two | Step One | Step Two |
|---|---|---|---|---|
| Phthalic Acid | 23.7 | 77.4 | 26.4 | 86.9 |
| Water | 0.2 | 1.1 | 8.3 | 3.4 |
| o-Xylene | 14.1 | 0.06 | 6.54 | Trace |
| Benzoic Acid | 9.91 | 9.07 | 8.38 | 7.84 |
| o-Toluic Acid | 24.8 | 1.5 | 31.0 | 0.13 |
| Phthalide | 5.99 | 0.8 | 7.51 | 0.07 |
| 2-CBA | 1.56 | | 2.16 | 0.05 |
| o-Tolualdehyde | 1.17 | 0.037 | 2.06 | Trace |
| High Boiler | 5.25 | 4.25 | 3.98 | 3.4 |
| Accountability | 85.1% | 94.2% | 96.3% | 100.4% |
| Mole % Burned | 7.4 | 4.7 | 5.0 | 5.0 |

(From The Invention Disclosure)

TABLE XII

| Description: | |
|---|---|
| Example | 3 |
| Step One Conditions | |
| Pressure, kg/cm$^2$ G | 28.1 |
| Temperature °C. | 165.6 |

TABLE XII-continued

| Description: | |
|---|---|
| O$_2$ in Exhaust, vol. % | 2.5 |
| o-Xylene Feed, g/min. | 108.2 |
| Cat. Comp./g. mole feed | |
| Co, milligram atom | 1.44 |
| Mn, milligram atom | 0.77 |
| Br, milligram atom | 4.24 |
| Air Rate, nl/min. | 209.6 |
| Residence Time, min. | 54 |
| Step Two Conditions | |
| Pressure, kg/cm$^2$ G | 28.1 |
| Temperature °C. | 212.8 |
| O$_2$ in Exhaust, vol. % | |
| Feed rate, g/min. | 30.65 |
| Cat. Comp./g. mole feed | |
| Co, milligram atom | 2.25 |
| Mn, milligram atom | 4.24 |
| Br, milligram atom | 10.2 |
| Air Rate, nl/min. | 66.1 |
| Reaction Time, min. | 165 |

| Product Analysis, wt. % | Step One | Step Two |
|---|---|---|
| Phthalic Acid | 22.96 | 86.0 |
| Water | 6.1 | 6.6 |
| o-Xylene | 10.6 | 0.01 |
| Benzoic Acid | 0.56 | 0.58 |
| o-Toluic Acid | 38.03 | 0.94 |
| Phthalide | 6.64 | 0.65 |
| 2-CBA | 1.46 | 0.14 |
| Tolualdehyde | 2.53 | 0.02 |
| High Boiler | 2.40 | 1.7 |
| Accountability | 91.6% | 96.9% |

The processes of Examples 1, 2, and 3 of the foregoing tables, which are illustrative of the best mode presently contemplated at the filing date hereof for the conduct of the present invention process, did produce respectively 147.7, 149.5, and 146.6 grams of o-phthalic acid per minute representing yields of 86, 87, and 86.5 percent (mole) of the theoretical yields possible from the o-xylene fed to the first steps.

A more complete analysis of the fluid reaction effluent resulting from the preferred (best mode) conduct of the present two-step neat oxidation of o-xylene with air is presented in TABLE XIII. Such analysis is on a water-free basis.

TABLE XIII

COMPONENTS
OF WATER-FREE SECOND STEP EFFLUENT

| Component, wt. % | |
|---|---|
| o-Phthalic Acid | 88.8 |
| Benzoic Acid | 2.05 |
| o-Toluic Acid | 0.82 |
| Phthalide | 0.86 |
| 2-Carboxybenzaldehyde | 0.54 |
| Dicarboxybenzophenone | 0.68 |
| Methyl Dicarboxybenzophenone | 0.88 |
| Tricarboxybenzophenone | 0.83 |
| Other High Boilers | 1.54 |
| Cobaltous Acetate | 0.83 |
| Manganous Acetate | 1.90 |
| Bromine (HBr) | 0.31 |

The foregoing two-step simulation neat oxidations of liquid o-xylene establish, it is submitted, that high accountability of products in the effluents from each step, high o-phthalic acid yields and rather high composition of the oxidation, (i.e., low yields of precursors) of o-phthalic acid are possible as long as the oxidation steps are conducted within the operating parameters defining the present invention. For example, Examples H, B, C, M, N, O, R, and T (batchwise oxidation of effluent produced by continuous first-step oxidation) produce high o-phthalic acid yields, high products accountability and high completion of conversion under conditions of a second step oxidation but simulated by batchwise operation. The results of illustrative (continuous first and second step oxidations) of Examples No. 1, No. 2 and No. 3 confirm the trends of high yield, accountability and completion of oxidation set by the simulated two-step oxidations.

The oxidations of Examples F, H, J demonstrate that operation of the second step under dry (too low water) conditions results in incomplete second step oxidation as well as low accountability and high phthalic anhydride concentrations.

It is also to be noted that the conduct of the first step can with respect to water content of reaction medium, be outside the limits defining the present inventive process but still good accountability from the second step, high yields and high completeness of oxidation (Examples I, L, T and W) can be achieved by operating the second step to correct and keep the water concentration within the parameters of the second step. The first step oxidation is less sensitive to high water content of the reaction medium and as long as the water content of the second step is properly adjusted (compare Examples T and U and No. 2) good complete oxidation can result. But, as Examples D, R and V indicate, the second step is quite sensitive to the presence of excess water.

The foregoing examples are presented as aids for the understanding and guidance for the practice of the present invention and are not intended as a limitation on our intended or understood scope of the present invention. Rather the scope of the present invention will be ascertained from the claims to follow.

The invention claimed is:

1. The continuous production of o-phthalic acid by the neat oxidation of liquid o-xylene with air in the presence of catalysis provided by a source of bromine and a source of cobalt and manganese as metal oxidation catalysts conducted in two consecutive steps wherein liquid xylene is charged to the first step; improved by the continuous addition of air, o-xylene, and said components of catalysis to a first stirred oxidation zone operated at a temperature from 160° C. up to 205° C. at a gauge pressure to maintain a liquid phase of the reaction mixture and to maintain therein a water content of from about 0.5 and up to 8 weight percent at said temperature, at a concentration of components of catalysis consisting essentially of from 1.0 up to 10 milliatoms of cobalt per gram mole of o-xylene and for each gram atom of cobalt from 0.5 up to 3 gram atoms of manganese and from 1 up to 10 gram atoms of bromine, and at a residence time such that the total of carbon oxides produced in the first zone is less than 5 mole percent of the xylene charged and the liquid reaction mixture contains o-xylene in the concentration of from 6 up to 30 weight percent and from 8 up to 40 weight percent o-phthalic acid; and directly adding such liquid reaction mixture together with air continuously to a second stirred reaction zone operated at a temperature from 210° C. up to 227° C. at a guage pressure to maintain in the liquid phase o-phthalic acid having a water content of from 2.5 up to 7 weight percent, at a concentration of components of catalysis based on each gram mole of o-xylene charged to the first oxidation zone consisting essentially of a total of from 1.18 up to 8 milligram atoms of cobalt and for each gram atom of cobalt from 0.5 up to 4 gram atoms of manganese and from 2 up to 10 gram atoms of bromine, and at a residence time such that liquid reaction mixture has a phthalide concentration not exceeding 0.1 weight percent of the o-phthalic acid and the total of carbon oxides produced in the second zone is less than 5 mole percent of the o-xylene charged to the first oxidation zone, wherein the source of bromine in each of the two oxidation zones is elemental bromine, hydrogen bromide, ammonium bromide or a bromide of cobalt or manganese.

2. The continuous process of claim 1 wherein the continuous addition of air, o-xylene and said components of catalysis to the liquid phase in the first stirred oxidation zone operated at a temperature in the range of from 160° C. up to 205° C., at a gauge pressure in the range of from 17 kg/cm$^2$ up to 30 kg/cm$^2$, with a ratio of air to o-xylene to provide a spent air exhaust containing oxygen in an amount of from 2 up to 15 volume percent, with the components of catalysis to provide from 1.0 up to 10 milligram atoms of cobalt per gram mole of o-xylene and for each 1.0 gram atom of cobalt from 0.5 up to 3 gram atoms of manganese and from 1 to 10 gram atoms of bromine, with a water content in the liquid phase of from 0.5 up to 8 weight percent, and with a residence time such that the o-xylene content of the liquid reaction mixture is in the range of from 6 up to 30 weight percent and the o-phthalic acid content concentration is in the range of from 8 up to 40 weight percent; and directly adding such liquid reaction mixture and air continuously to a second stirred reaction zone operated at a temperature in the range of from 210° C., up to 227° C., at a gauge pressure in the range of from 27 kg/cm$^2$ up to 35 kg/cm$^2$, with a ratio of air to liquid reaction mixture to provide a spent air exhaust containing oxygen in an amount of from 7 up to 10 volume percent, with components of catalysis such that the total cobalt based on o-xylene charged to the first oxidation zone is from 1.2 up to 8 milligram atoms of cobalt per gram mole of said o-xylene and for each 1.0 gram atom of such total cobalt from 0.5 up to 4 gram atoms of manganese and from 2 up to 10 gram atoms of bromine, with from 2.5 up to 7 weight percent water in the liquid reaction mixture in the second oxidation zone, and with a residence time such that the liquid reaction mixture has a phthalide content not exceeding 0.1 weight percent of the o-phthalic acid present.

3. The continuous process of claim 2 wherein the concentration of cobalt to o-xylene added to the first oxidation zone is in the range of from 0.5 to 1.0 milligram atoms per gram mole of o-xylene, the ratio of cobalt to manganese to bromine is in the respective gram atom ratio of 1:0.5–2.0:4, and said oxidation zone is operated at a temperature of from 168° C. up to 171° C., at a gauge pressure of from 27.5 up to 32 kg/cm$^2$, at a water concentration in the liquid reaction mixture of from 2 up to 5 weight percent, and at a residence time of from 40 up to 60 minutes.

4. The process of claim 3 wherein the spent air from the first oxidation zone has an oxygen content of from 2 up to 10 volume percent.

5. The continuous process of claim 3 wherein the concentration of cobalt in the second oxidation zone is from 1.2 to 3.5 milligram atoms per gram mole of o-xylene charged to the first oxidation zone, the ratio of cobalt to manganese to bromine is in the respective gram atom range of 1:2–3:3–5, and the second oxidation zone is operated at a temperature in the range of from 205° C. up to 215° C., at a gauge pressure of from 27 up to 31 kg/cm$^2$, at a water concentration in the liquid reaction mixture of from 3 up to 6 weight percent, and at a residence time of from 2 up to 4 hours.

6. The process of claim 5 wherein the spent air from the second oxidation zone has an oxygen content of from 7 up to 10 volume percent.

7. The process of claim 4 wherein the cobalt and manganese components of catalysis added to the first oxidation zone are provided by salts thereof soluble in the reaction mixture and the source of bromine is Br$_2$ added separately to the liquid reaction mixture.

8. The process of claim 4 wherein the source of cobalt and manganese and bromine added to the first oxidation zone are acetates of cobalt and manganese and the source of bromine is hydrogen bromide and wherein both sources are dissolved in water.

9. The process of claim 4 wherein the o-xylene added to the first oxidation zone contains benzoic acid in an amount of from 3 up to 10 weight percent.

10. The process of claim 2 wherein the heat of reaction in the first oxidation zone is removed by indirect exchange between the liquid reaction mixture and a heat exchange fluid.

* * * * *

UNITED STATES PATENT OFFICE
CERTIFICATE OF CORRECTION

Patent No. 4,387,243          Dated June 7, 1983

Inventor(s) Houssam M. Naim, Nicholas C. Huie and George E. Kuhlmann

It is certified that error appears in the above-identified patent and that said Letters Patent are hereby corrected as shown below:

| Column | Line | |
|---|---|---|
| 1 | 55 | "devices" should read --devises-- |
| 5 | 36 | "liquod" should read --liquid-- |
| 7 | 7 | "mixture," should read --mixture-- |

Signed and Sealed this

Twenty-fourth Day of January 1984

[SEAL]

Attest:

GERALD J. MOSSINGHOFF

Attesting Officer          Commissioner of Patents and Trademarks